United States Patent [19]
Osipow et al.

[11] Patent Number: 4,744,979
[45] Date of Patent: May 17, 1988

[54] SELF-LATHER GENERATING SHAVING COMPOSITION

[76] Inventors: Lloyd I. Osipow, 2 Fifth Ave, New York, N.Y. 10011; George Spitzer, 44 Coconut Row, Palm Beach, Calif. 33480; Dorothea C. Marra, 107 Fernwood Rd., Summit, N.J. 07901

[21] Appl. No.: 903,903

[22] Filed: Sep. 4, 1986

Related U.S. Application Data

[63] Continuation of Ser. No. 679,222, Dec. 7, 1984, abandoned.

[51] Int. Cl.⁴ .............................................. A61K 7/15
[52] U.S. Cl. ...................................... 424/73; 514/945
[58] Field of Search .......................................... 424/73

[56] References Cited

U.S. PATENT DOCUMENTS

| | | |
|---|---|---|
| 2,908,650 | 10/1959 | Fine ........................................ 424/73 |
| 3,639,568 | 2/1972 | Schmitt .................................. 424/49 |
| 4,035,477 | 7/1977 | Schubert et al. ...................... 424/73 |
| 4,088,751 | 5/1978 | Kenkare et al. ...................... 424/73 |
| 4,145,411 | 3/1979 | Mende .................................... 424/73 |

FOREIGN PATENT DOCUMENTS

| | | | |
|---|---|---|---|
| 719647 | 12/1954 | United Kingdom ................... | 424/73 |
| 838913 | 6/1960 | United Kingdom ................... | 424/73 |

OTHER PUBLICATIONS

McCutcheon's, *Detergents & Emulsifiers*, pp. 37–58 (1971).
*Merck Index*, 9th ed, abst. a#1497, 4563, 6913 (1976).

Primary Examiner—Jerome D. Goldberg
Assistant Examiner—F. Krosnick
Attorney, Agent, or Firm—Morgan & Finnegan

[57] ABSTRACT

A shaving preparation is provided which has a sub-atmospheric vapor pressure at ambient temperature and which generates a lather when applied to the skin. The composition comprises a water-insoluble volatile organic liquid having a vapor pressure substantially below atmospheric pressure, an aqueous soap solution and a surface active agent which together promote the volatilization of the organic liquid, thereby generating a lather as well as reducing the tendency of the volatile organic liquid to cause smarting of the skin. The compositions of this invention are capable of being packaged in a collapsible tube without premature expansion in the tube during storage, shipment and use.

24 Claims, No Drawings

SELF-LATHER GENERATING SHAVING COMPOSITION

This is a continuation of co-pending application Ser. No. 679,222, filed on Dec. 7, 1984 now abandoned.

BACKGROUND OF INVENTION

Compositions that produce lather for shaving have been known for many decades. One type of known shaving composition that have been used for years are those whisked with a brush to incorporate air and thereby generate lather.

Another type of known lather producing shaving composition are those aerosol shaving compositions containing volatile organic liquids under super atmospheric pressure. Such compositions are disclosed in U.S. Pat. No. 2,655,480 to Spitzer et al. In these lather producing compositions, the vapor pressure of the volatile liquids is substantial, say 25 to 40 p.s.i.g. so that the compositions are immediately converted to lather when released from the aerosol container to the atmosphere.

A more recent type of lather producing shaving composition is the gel lather producing composition disclosed in U.S. Pat. No. 3,541,581 to Monson. In the composition of this patent there are employed organic liquids with vapor pressures of 6 to 14 p.s.i.g. According to Monson patent, the Monson compositions when released from their container would quickly expand to a lather if not for the inclusion of a gelling agent which restrains lather formation until the shaving composition is applied to the skin in the form of a gel.

More particularly, the Monson compositions are postfoaming shaving gel compositions that are dispensed as gels, but produce a lather when rubbed on the face. The compositions comprise a soap solution, a gelling agent, and an organic liquid having a vapor pressure from about 6 to about 14 p.s.i.g. at a temperature from about 90° to 100° F. The organic liquid is the post-foaming agent.

In order to dispense Monson's compositions with their super-atmospheric vapor pressures in the form of gels, it is necessary to employ an especially complex and expensive-aerosol container, that in addition to the usual components also includes a bag or piston or equivalent device, as shown in Monson's FIG. 4 of the Monson patent.

While Monson states that his post-foaming gels can be packaged in collapsible metal tubes, this is not practical. Because of the super-atmospheric pressure of the compositions, it is necessary to use an aerosol valve and dispensing spout. If a tube cap were used, the composition would continue to gush from the container until the cap were screwed into place. Further, the crimped end of the collapsible tube would unravel and pop open under the sustained pressure of the composition. In addition, the pressure would maintain the collapsible metal tube in a constantly expanded state, regardless of the amount of material in the tube. As a consequence, as the contents were emptied, the gel would tend to expand to fill the tube, and then be expelled as an aerated gel or lather.

The Monson compositions because of their above atmospheric vapor pressure can not be exposed to elevated temperature in storage, shipping and use without causing problems of premature expansion.

OBJECTS OF THE INVENTION

It is widely recognized that important functions of shaving compositions include wetting of the beard, followed by softening of the beard as a consequence of its imbibing the aqueous solution. Lubrication of the beard and the skin is an additional important function. The wetting and softening actions are favored where the composition is in a sufficiently mobile form (liquid, gel, cream and the like) to spread and penetrate the beard, rather than being immobilized in the walls of a lather. Consequently, it is advantageous to apply the composition in liquid form and for it to remain thus for a finite period of time, rather than applying it as a lather. Wetting and softening actions are further enhanced by rubbing the mobile shaving composition into the beard. Ideally, lather generation should be delayed for the small period required to effectively soften the beard, but the delay should not be excessive. An object of this invention is to provide a shaving composition in mobile form that can be rubbed into the skin and beard and thereby generate a lather. A further object is to control the time required for the lather to be generated to insure thorough softening of the beard, but without excessive delay.

It is an object of this invention to provide shaving compositions with sub-atmospheric vapor pressures that generate a lather when rubbed on the face.

A further object of this invention is to provide shaving compositions with sub-atmospheric vapor pressures that generate a lather when rubbed on the face and which may be economically packaged in inexpensive containers such as, for example, collapsible tubes.

Another object of this invention is to provide shaving compositions with sub-atmospheric vapor pressures that generate a lather when rubbed on the face and which may be exposed to elevated temperature in storage, shipping and use without premature expansion of the composition occurring.

A still further object of this invention is to provide shaving composition wherein the vapor pressures of the compositions do not exceed atmospheric pressure at about 100° F., and preferably up to about 120° F. so that they may be exposed to elevated temperatures in storage, shipping and use without premature expansion occurring.

Another object of this invention is to provide shaving compositions with sub-atmospheric vapor pressure which when applied to the skin does not tend to impart a smarting sensation therefore.

A still further object of this invention is to provide a relatively inexpensive shaving composition package in the form of a collapsible tube containing a shaving composition with sub-atmospheric vapor pressures that generate a lather when rubbed on the face and which does not cause premature expansion thereof in the container when exposed to storage, shipping and use conditions including elevated temperatures e.g. 100 F. and preferable up to 120 F.

GENERAL DESCRIPTION OF THE INVENTION

It has been found that the objects of this invention may be realized by providing a shaving composition comprising a volatile organic liquid in liquid form at normal ambient temperature having a vapor pressure substantially below atmospheric pressure combined with an aqueous soap solution and a surface active agent, said soap solution and surface active agent capable of promoting the volatilization of the organic liquid thereby generating a lather in a practical period of time e.g., less than about 15 seconds, as well as reducing smarting.

Prior to the present invention it would not have been expected that a shaving composition employing an organic liquid having a vapor pressure substantially below atmospheric pressure could produce sufficient gas in a practical period of time to generate a shaving lather. More particularly, the use of organic liquids with vapor pressure substantially below atmospheric was not previously contemplated by the prior art because it was improbable that such liquids could evolve sufficient gas in a practical period of time for a shaving lather. In fact, it could not be done prior to this discovery that certain aqueous soap solutions promote the volatilization of those liquids to a sufficient extent that a lather may be generated in a practical period of time. For example, it has now been found that when a mixture of saturated hydrocarbons having a vapor pressure of about 5 p.s.i.a. at 20° C. is combined with a soap solution of this invention and applied to the face it will generate a stable shaving lather when rubbed for only a few strokes. In contrast, using the same organic liquid with a conventional soap solution considerably more rubbing would be required.

The essential components of the invention, i.e., the aqueous soap solution; the surface active agent; and, the water-insoluble volatile organic liquid having a vapor pressure substantially below atmospheric will now be discussed in detail.

A. AQUEOUS SOAP SOLUTION

As indicated earlier the aqueous soap solution is of such nature and is in such an amount that when it is combined with the surface active agent the volatilization of the volatile organic liquid is promoted to the extent that when the composition is rubbed on the skin a lather is generated within a practical period of time, e.g., less than about 15 seconds.

Example of aqueous soap solution useful in this invention are aqueous solutions of water-soluble palmitate or stearate soaps of sodium, potassium, ammonium, morpholine, and various alkanolamines, such as mono-, di-, and triethanolamine, mono-, di-, and triisopropanolamine, and 2-amino-2methyl-1-propanol, and mixtures of these water-soluble soaps. Preferably the soaps are superfatted, usually with free fatty acids, to aid the stability of the lather. With strong alkalis it is preferable to neutralize using only about 60 to 90% of the stoichiometric equivalent amount of alkali, to assure sufficient superfatting. With weak alkalis, such as triethanolamine, free fatty acids are present even when the stoichiometric equivalent amount of amine is used.

These soaps are preferably prepared in situ by the neutralization of the fatty acids with alkali. They may also be prepared by alkaline saponification of a fat, such as tallow or hydrogenated corn oil.

In general, the aqueous solution should contain soap plus superfatting agent, wherein the soap plus superfatting agent is in an amount of about 5 to 25% by weight of the total composition. At least 60% by weight of this amount should be soap. If the amount of soap plus superfatting agent is too low, the lathers generated will lack stability; if too high, it will interfere with lather formation. If the soap content is less than about 60% of the combination of soap and superfatting, lather formation will be adversely affected. The preferred amount of soap and superfatting is from about 7 to about 14% by weight of the total composition.

While the fatty acids remaining after incomplete neutralization are the preferred superfatting ingredients, other water-insoluble long chain polar compounds may be used, such as cetyl alcohol, stearyl alcohol, lanolin alcohols, cetyl amide, glyceryl monopalmitate, glyceryl monostearate, propylene glycol monopalmitate and propylene glycol monostearate.

B. THE SURFACE ACTIVE AGENT

The surface active agent is of such nature and is in such an amount that when combined with the aqueous soap solution the volatilization of the volatile organic liquid is promoted to the extent that when the composition is rubbed on the skin a lather is generated within a practical period of time.

Examples of suitable surface active agents are nitrogen-containing surface active agents that are nonionic in alkaline media and cationic in acid media, selected from the group consisting of:

(a) Tertiary amine oxides with one long hydrocarbon chain of 12 to 22 carbon atoms. Examples of suitable materials include lauryl dimethyl amine oxide, myristyl dimethyl amine oxide, cetyl dimethyl amine oxide, stearyl dimethyl amine oxide, lauryl morpholine amine oxide, bis (2-hydroxyethyl) lauryl amine oxide, and bis (2-hydroxyethyl) stearyl amine oxide; and, (b) lauroyl and myristoyl alkanolamides, such as lauroyl diethanolamide, myristoyl diethanolamide, lauroyl monoethanolamide, and lauroyl diisopropanolamide.

These amine oxides and alkanolamides, when combined with aqueous soap solutions and suitable volatile organic liquids, have the effect of increasing the ease with which a shaving lather is generated by rubbing on the skin. Since lather formation requires the evolution of a sufficient amount of gas due to volatilization of the organic liquid, it follows that these compounds promote the volatilization of the organic liquid. They also reduce smarting, in part due to the more rapid volatilization of the organic liquid.

The amine oxides are the preferred nitrogen-containing surface-active agents. Larger amounts can be used than the alkanolamides, and consequently, more rapid lather formation can be achieved. In general, the amine oxides do not reduce the viscosities of the alkanolamine soap solutions and may enhance their viscosities. They tend to reduce the viscosities of sodium and potassium soap solutions.

The alkanolamides are comparable to the amine oxides at low concentrations in their effectiveness in promoting lather generation. However, at higher concentrations they have the unusual effect of producing a pituitous lather. Further rubbing after the lather has been formed causes the lather to constrict to a cluster, pulling away from the skin. This is an unsatisfactory effect. When used at low concentration, either alone or in combination with the amine oxides, the alkanolamides are effective in increasing the viscosities of soap solutions as well as in promoting lather formation.

The amine oxides and alkanolamides can be used at concentrations ranging from about 1 to about 10% by weight of the composition. The preferred concentration range is from about 2% to about 8% by weight of the composition. They may be used alone or in combination. However, the alkanolamides should generally not be used at concentrations greater than about 3% by weight.

C. Volatile Organic Liquid

The volatile organic liquid is of such nature and in such amount that, although in liquid form at ambient temperature and having a vapor pressure substantially below atmospheric pressure, its volatilization is capable of being promoted by the combination of the aqueous soap solution and the surface active agent to an extent that a lather is generated in a practical period of time.

The volatile organic liquid is a water-insoluble organic liquid boiling in the range from about 25° C. to about 70° C., but preferable in the range from about 35° C. to about 50° C. Those liquids include saturated aliphatic hydrocarbons having 5 or 6 carbon atoms, such as n-pentane, iso-pentane, n-hexane, iso-hexane, 2,2-dimethyl- butane, 2,3-dimethyl-butane, and 3-methyl-pentane, and completely halogenated hydrocarbons containing 2 carbon atoms such as 1,1,2-trichloro-trifluoroethane.

A single ingredient or a blend of two or more ingredients may be used to obtain the required boiling point. The compounds with lower boiling points may also be blended with ingredients that will dissolve in them and which have substantially higher boiling points, for the purpose of raising the boiling point of the more volatile organic liquid. Examples of such ingredients include superfatting agents, such as the higher fatty acids and higher fatty alcohols and monoglycerides, emollients, such as mineral oils, lanolin, and esters of the higher fatty acids, and hydrocarbons of intermediate boiling points such as decane and dodecane.

Organic liquids that are more water-soluble than the saturated aliphatic hydrocarbons and the completely halogenated hydrocarbons reduce lather stability and also tend to increase smarting. They are preferably not used, except in minor amounts.

The aliphatic hydrocarbons are used at a concentration of at least about 1% and preferably from about 2 to about 5% of the composition, while the halogenated hydrocarbons will comprise at least about 2% and preferably from about 3 to 8% of the composition.

D. Adjuvant Ingredients

In addition to these essential components, various adjuvant ingredients customarily used in shaving preparations may be incorporated. These include humectants, such as glycerine, propylene glycol and sorbitol, emollients such as lecithin and lanolin, corrosion inhibitors such as sodium and potassium silicates, preservatives such as the methyl and propyl esters of p-hydroxybenzoic acid, dyes, and fragances.

The amine oxides and the alkanolamides used in the practice of this invention are commonly used in combination with anionic surface active agents to stabilize foam in the presence of soil. Detergent solutions containing these ingredients in combination with anionic detergents will exhibit foaming action in the presence of larger amounts of soil than without these ingredients. Similarly, they may be used in shaving preparations to stabilize the lather in the presence of natural oils present on the skin. Prior to the present invention, it was neither known nor contemplated that these foam stabilizers would be useful in promoting the volatilization of volatile organic liquids, thereby facilitating lather formation. Neither was it known or contemplated that these ingredients would be effective in reducing the smarting of these volatile organic liquids in soap solutions.

The effect of alkanolamides and amine oxides in increasing the rate of vaporization of organic liquids is illustrated by the following examples using n-hexane as the organic liquid. N-hexane boils at 69° C. and has a vapor pressure of only 2.5 p.s.i.a. at 21° C. and 5.0 p.s.i.a. at 38° C. (100° F.). The soap solution used in the test comprised 10.5% monoethanolamine palmitate, with 70% of the fatty acid neutralized by the amine, 4.7% sorbitol, and 84.8% water. The additives were combined with the soap solution and then 5% by weight of n-hexane was mixed in.

The samples were evaluated by stroking in a circular motion on the wet inner forearm of a subject until a shaving lather was generated. The results in Table 1 show that the use of an appropriate additive could reduce the number of strokes required to produce a lather to less than ½, and sometimes less than ¼ the number of strokes required for a soap solution without additive.

TABLE 1

| Additive | | Required Number of Strokes For Lather Formation |
|---|---|---|
| A. | None | 115 |
| B. | 1.25% Lauroyl diethanolamide (97% pure) | 55 |
| C. | 1.25% Lauroyl diethanolamide (97% pure) + 1.5% lauryl dimethyl amine oxide | 25 |
| D. | 1.5% Lauryl dimethyl amine oxide | 40 |
| E. | 3.0% Lauroyl diethanolamide (97% pure) | 40 |
| F. | 3.0% Lauroyl diethanolamide (97% pure) + 1.5% lauryl dimethyl amine oxide | 30 |
| G. | 2.0% Cetyl dimethyl amine oxide | 30 |
| H. | 2.0% Stearyl dimethyl amine oxide | 30 |
| I. | 2.0% Myristyl-cetyl dimethyl amine oxide | 30 |
| J. | 2.0% Coco-amido propyl dimethyl amine oxide | 40 |

The examples that follow were prepared in essentially the same way. The fatty acids, alkali, humectant and water were combined and heated to 80° to 85° C. with slow stirring. The soap solution was cooled under vacuum, with slow stirring, to 45° C. Concentrated solutions, about 30% by weight, of the amine oxide and alkanolamide were then added, along with preservatives, corrosion inhibitors, fragances, and most other ancillary agents. Any ancillary waxes are best added initially. After thes additions, the composition is cooled with slow stirring under vacuum to ambient temperature. The volatile organic liquid is then added and mixed in with slow stirring. Pressure is then applied to the vessel to facilitate filling into collapsible tubes. Vacuum is used during the preparation to minimize air entrapment.

It is advantageous to remove air from the head space in the tube. This is conveniently done by drawing a vacuum on the tube after filling, and before final sealing of the tube. If the air is not removed from the head space, the pressure in the tube will be above atmospheric, and this can result in leakage, unfolding of a crimp or the rupture of a heat seal.

The compositions may be packaged in any type of collapsible tube that has a sufficiently good barrier layer to prevent loss of the volatile organic liquid through the walls of the tube. Thus, they may be packaged in aluminum, coated aluminum, tin-plate, coated tin-plate, wax-lined lead, and laminated tubes with an appropriate barrier layer.

While it is considered preferable to prepare the compositions as gels or creams, suitable for packaging in tubes, they may also be prepared as viscous liquids, clear or opaque, and packaged in bottles. Glass or plastic bottles may be used, provided the material selected is a sufficient barrier to prevent loss of the volatile organic liquid through the walls.

SPECIFIC DESCRIPTION OF THE INVENTION

The following Examples illustrate the invention. In all of the examples, the same method was used to evaluate the ease with which a lather could be generated by rubbing, as described in Example 1. In all instances, comparison is made with a control, which differs from the example essentially in that the amine oxide and/or alkanolamide was omitted. The vapor pressures are calculated and do not take into consideration any pressure lowering effect due to the free fatty acids. The actual vapor pressures can be expected to be a little lower than the values shown in the examples.

EXAMPLE 1

This example illustrates the effect of the alkanolamide and amine oxides in improving the ease with which a lather is generated and in reducing smarting using a potassium palmitate soap, with the fatty acids 70% neutralized.

| Soap Solution | Parts by Weight |
|---|---|
| Palmitic acid | 40.4 |
| Potassium hydroxide | 6.2 |
| Propylene glycol | 20.0 |
| Water | 360.0 |

The ingredients were combined, heated to the boil, and then cooled using slow-speed stirring throughout.

| Composition 1 | Parts by Weight |
|---|---|
| Soap solution (as above) | 123.0 |
| Lauroyl diethanolamide | 4.5 |
| 30% Lauryl dimethylamine oxide in water | 22.5 |
| n-Pentane | 6.0 |

Control A was prepared by blending 4% by weight of n-pentane into the soap solution. Both Composition 1 and Control A were packaged in collapsible aluminum tubes and evaluated the following day.

Comparison was made between the number of strokes required to generate a lather with the two samples by rubbing with a circular motion on a wet inner forearm. Control A, which was an opaque cream required 23 strokes to generate a lather, which was of good stability. Composition 1, which was a transparent gel, required only 8 strokes to generate a lather, which was also of good stability.

Small globs of about equal size of the two samples were placed on each arm of a subject, and allowed to stay undisturbed for 5 minutes before removing. On both arms, Control A produced smarting and redness, while Composition 1 did not.

EXAMPLE 2

This Example is similar to the previous one, except that an amine soap is used in place of a potassium soap. Again, the fatty acids wre 70% neutralized.

| Soap Solution | Parts by Weight |
|---|---|
| Palmitic acid | 40.2 |
| monoethanolamine | 6.8 |
| Sorbitol | 20.0 |
| Water | 360.0 |

The ingredients were combined, heated to the boil, and then cooled using slow-speed stirring throughout.

| Composition 2 | Parts by Weight |
|---|---|
| Soap solution (as above) | 130 |
| 30% Lauryl dimethylamine oxide in water | 20 |
| n-Pentane | 6 |

Control B was prepared by blending 4% by weight of n-pentane into the soap solution. Composition 2 and Control B were packaged in aluminum tubes and evaluated. Control B was a pearlescent cream, while Composition 2 was a transparent gel.

When rubbed on a web inner forearm, Control B required 20 strokes to generate a lather, while Composition 2 only required 9 strokes. When applied to the face, worked into a lather, and then left on for 3 minutes, only Control B produced smarting.

| | Examples | | | | |
|---|---|---|---|---|---|
| | 3 | 4 | 5 | 6 | 7 |
| | Parts by Weight | | | | |
| Palmitic acid | 4.2 | 6.8 | 4.5 | 7.9 | 7.9 |
| Stearic acid | 2.7 | 1.6 | 3.6 | — | — |
| Sodium hydroxide | 0.8 | 0.5 | — | — | — |
| Potassium hydroxide | — | 0.5 | — | — | — |
| Monoethanolamine | — | — | — | 3.2 | 1.3 |
| Diethanolamine | — | — | 2.3 | — | — |
| Lauroyl diethanolamide | — | 2.4 | 2.3 | — | — |
| Lauryl dimethyl amine oxide | 6.0 | 4.0 | — | 3.7 | — |
| Cetyl dimethyl amine oxide | — | — | 2.3 | — | 3.6 |
| Propylene glycol | 3.8 | 4.3 | — | — | — |
| Sorbitol | — | — | 4.0 | 3.9 | 3.9 |
| Water | 79.0 | 75.2 | 77.1 | 79.0 | 79.6 |
| n-Pentane | 3.4 | 3.8 | 4.0 | 4.2 | 3.8 |
| n-Hexane | — | — | — | — | 0.8 |
| Isopar E* | — | 0.8 | — | — | — |
| Calculated vapor pressure at 21°p.s.i.a. | 8.5 | 7.7 | 8.5 | 8.5 | 7.6 |
| Strokes Required for lather | 10 | 17 | 8 | 10 | 15 |
| Strokes required for lather with control | 20 | 40 | 23 | 25 | 35 |

*Isopar E (Exxon) - isoparaffinic hydrocarbon fraction composed principally of 8-carbon isomers, 116–139° C. boiling range; ave. mol. wt. - 128

The following Examples 8 and 9 illustrate compositions that include corrosion inhibitor, preservatives and perference. These compositions are in the form of gels, which is the preferred form of the invention.

| | Parts by Weight | |
|---|---|---|
| Example | 8 | 9 |
| Palmitic acid | 5.7 | 7.8 |
| Coconut fatty acids | 0.7 | — |
| Triethanolamine | 2.9 | — |
| Monoethanolamine | — | 1.2 |
| Lauroyl diethanolamide | 2.8 | — |
| Lauryl dimethylamine oxide | 2.5 | 0.6 |
| Cetyl dimethylamine oxide | — | 3.2 |
| Sorbitol | 4.2 | 4.0 |
| Sodium Metasilicate | 0.2 | 0.4 |
| Methyl p-hydroxybenzoate | 0.2 | 0.2 |
| Propyl p-hydroxybenzoate | 0.1 | 0.1 |
| Perfume | 0.2 | 0.2 |

-continued

| Example | Parts by Weight | |
|---|---|---|
| | 8 | 9 |
| Water | 76.6 | 78.5 |
| n-Pentane | 3.9 | 3.8 |
| Calculated vapor pressure at 21° C., p.s.i.a. | 8.5 | 8.5 |
| Strokes required for lather | 5 | 4 |
| Strokes required for lather with control | 35 | 25 |

While the present invention is not limited to any specific theory of action, it should be of interest and might be helpful in understanding the invention if some possible explanation is offered for the surprising discovery that it is possible for shaving lather to be produced rapidly using volatile organic liquids having vapor pressures that are substantially below atmospheric pressure.

It appears likely that several factors acting in concert are responsible for the formation of lathers at a practical rate from the compositions of this invention. First, the organic liquid may be present in liquid droplets of very small size. It is known that droplets of small size have a larger vapor pressure than the bulk liquid. This is the case because condensation will increase the surface area, and therefore the surface free-energy of the system to a greater extent with small droplets than with large droplets. Similarly, evaporation will decrease the surface area and the surface free-energy of smaller droplets to a greater extent than with larger droplets.

The argument has validity if the droplets are at a vapor-liquid interface. At a liquid-liquid interface, the interfacial tension is apt to be quite low and the increase in the vapor pressure of the organic liquid due to its small droplet size could be minor.

Then the second requirement is that the small droplets be brought to the surface so that they are at least partially at a liquid-vapor interface. This can significantly increase the vapor pressure of the organic liquids. Rapid conversion of the organic liquid to gas is also aided by a large surface area. It is reasonable to speculate that rubbing the shaving composition onto the face initiates the process of rapid evaporation of organic liquid by first entrapping air to form tiny bubbles, thus enlarging the surface area. The organic liquid droplets migrate to the surface and the liquid vaporizes into the air bubbles causing the bubbles to grow larger. Further rubbing breaks down the bubbles into smaller ones, which further increases the surface area; also, more air is entrapped. The process feeds on itself, and with increased rubbing, the lather becomes thicker as more organic liquid is converted to gas.

The compositions used in the practice of this invention are demonstrably superior to the compositions of the prior art with regard to the ease with which they produce shaving lathers using volatile organic liquids of low vapor pressure. The above speculations suggest that this superiority is due to one or more of the following: formation of organic liquid droplets of smaller size; a greater tendency for these droplets to concentrate at the surface, a greater tendency to entrap air by rubbing, and the promotion of a larger surface area by forming smaller bubbles.

Another advantage of the compositions of this invention is that they have less tendency to cause smarting or irritation than conventional shaving soap solutions compounded with the same organic liquids. It can be readily shown that these organic liquids, when in liquid form, do have a tendency to cause smarting or stinging. Since these organic liquids are more readily converted to gaseous form with the soap solutions of the invention than with those of the prior art, this reduced tendency towards smarting is readily understood. However, this is only part of the picture. When the comparison compositions are placed on the skin and allowed to remain undisturbed, very little volatilization of organic liquid occurs from either mass, yet irritation and redness may be observed from the prior art soap solution, but not from the soap solution of the invention. It may be that the layer of soap and other surface-active molecules that surround the organic liquid droplet are more effective as barriers to screen the droplets from contact with the skin. It is known, for example, that anionic detergents such as soaps form expanded surface films. When superfatted, the surface films become more condensed as a consequence of ion-dipole interaction between the long-chain soap anion and the fatty acid dipole. Neutral nitrogen-containing surface active agents, such as the amine axides and alkanolamides, interact particularly strongly with soap anions to give more tightly packed surface films that may be responsible for this proposed barrier effect.

What is claimed is:

1. A shaving preparation having a sub-atmospheric vapor pressure at ambient temperatures and which generates lather in a practical period of time when applied to the skin consisting essentially of (1) an aqueous soap solution; (2) a surface active agent; and, (3) a volatile water-insoluble organic liquid having a vapor pressure substantially below atmospheric pressure, and capable of having its volatilization promoted by the aqueous soap solution and surface active agent, said aqueous soap solution and surface active agents being of such nature and in such amounts that when said compositions is applied to the skin the volatilization of the volatile organic liquid is promoted to the extent that a lather is generated in a practical period of time while reducing the tendency of the volatile organic liquid to cause smarting of the skin, said aqueous solution containing the surface active agent in an amount of about 1 to 10% by weight of the total composition and a water-insoluble volatile organic liquid in an amount of 1 to 10% by weight of the total composition, said aqueous solution containing soap in an amount from about 5 to 25% by weight; the water of the aqeuous solution being present in an amount to give 100% by weight for the composition.

2. A shaving preparation according to claim 1 wherein the soap is selected from the group consisting of water soluble plamitate and stearate soaps.

3. A shaving preparation according to claim 1 wherein up to 40% by weight of the soap has been replaced by a superfatting agent.

4. A shaving preparation according to claim 1 wherein the soap solution is superfatted with free fatty acids, the free fatty acids being in an amount up to 40% of the total weight of soap plus free fatty acids.

5. A shaving preparation according to claim 1 wherein the soap solution contains as the soap an alkanolamine palmitate soap with the fatty acids from about 60% to about 90% neutralized.

6. A shaving preparation according to claim 1 wherein the soap of the aqueous soap solution is selected from the group consisting of water soluble palmitate and stearate soaps of sodium, potassium, ammonium, morpholine and alkanolamines.

7. A shaving preparation according to claim 1 wherein the surface active agent is a nitrogen containing surface active agent that is nonionic when dissolved in soap solutions.

8. A shaving preparation according to claim 1 wherein the surface active agent is a nitrogen containing surface active agent selected from the group consisting of tertiary amine oxides with one long hydrocarbon chain of 12 to 22 carbon atoms and lauroyl and myristoyl alkanolamides.

9. A shaving preparation according to claim 1 wherein the surface active agent is selected from the group consisting of lauryl dimethyl amine oxide, myristyl dimethyl amine oxide and cetyl dimethyl amine oxide.

10. A shaving preparation according to claim 1 wherein the surface active agent is a tertiary amine oxide having a hydrocarbon chain of 12 to 22 carbon atoms.

11. A shaving preparation according to claim 1 wherein the surface active agent is a tertiary amine oxide having a hydrocarbon chain of 12 to 22 carbon atoms, said surface active agent being in an amount from 2 to 8% by weight.

12. A shaving preparation according to claim 1 wherein the volatile organic liquid boils in the range of about 25° C. to about 70° C.

13. A shaving preparation according to claim 1 wherein the volatile organic liquid boils in the range of about 35° C. to about 50° C.

14. A shaving preparation according to claim 1 wherein the volatile organic liquid is selected from the group consisting of saturated aliphatic hydrocarbons having 5 or 6 carbon atoms and completely halogenated hydrocarbons containing 2 carbon atoms.

15. A shaving preparation according to claim 1 wherein the volatile organic liquid is a saturated aliphatic hydrocarbon having 5 or 6 carbon atoms in an amount from about 2 to about 5% of the composition.

16. A shaving preparation according to claim 1 wherein the volatile organic liquid is a completely halogenated hydrocarbon containing 2 carbon atoms in an amount from about 3% to about 8% by weight of the composition.

17. A shaving preparation according to claim 1 wherein the volatile organic liquid is n-pentane.

18. A shaving preparation according to claim 1 where there is present a humectant.

19. A shaving preparation according to claim 1 wherein the humectant is selected from the group consisting of glycerine, propylene glycol and sorbitol.

20. A shaving preparation according to claim 1 wherein the soap of the soap solution is selected from the group consisting of water soluble palmitate and stearate soaps, the surface active agent is selected from the group consisting of tertiary amine oxides with one long hydrocarbon chain of 12 to 22 carbon atoms and lauroyl and myristoyl alkanolamides; and, the volatile organic liquid is selected from the group consisting of saturated aliphatic hydrocarbons having 5 or 6 carbon atoms and completely halogenated hydrocarbons containing two carbon atoms.

21. A shaving preparation according to claim 1 wherein the soap is selected from the group consisting of potassium, sodium, monoethanolamine diethanolamine and triethanolamine salts of palmitic acid and stearic acid; the surface active agent is selected from the group consisting of lauryl dimethyl amine oxide, myristyl dimethyl amine oxide cetyl dimethyl amine oxide and lauroyl diethanalamide; and, the volatile organic compound is n-pentane.

22. A shaving preparation accordng to claim 1 wherein there is present a humectant selected from the group consisting of propylene glycol and sorbitol.

23. A shaving preparation according to claim 1 wherein the soap of the soap solution is selected from the group consisting of alkanolamine palmitate and stearate soaps, with the fatty acids about 60 to 90% neutralized, the surface active agent is selected from the group consisting of tertiary amine oxides with one long hydrocarbon chain of 12 to 22 carbon atoms and lauroyl and myristoyl alkanolamides; and, the volatile organic liquid is selected from the group consisting of saturated aliphatic hydrocarbons having 5 or 6 carbon atoms and completely halogenated hydrocarbons containing two carbon atoms.

24. The shaving preparation according to claim 1 contained in a collapsible tube.

* * * * *

UNITED STATES PATENT AND TRADEMARK OFFICE
CERTIFICATE OF CORRECTION

PATENT NO. : 4,744,979

DATED : May 17, 1988

INVENTOR(S) : Lloyd I. Osipow; J. George Spitzer and
Dorothea C. Marra

It is certified that error appears in the above-identified patent and that said Letters Patent is hereby corrected as shown below:

Column 1, line 35, "postfoaming" should read --post-foaming--;
Column 6, line 48, "thes" should read --these--;
Column 10, line 20, "nigtrogen-containing" should read --nitrogen-containing--;
Claim 1, line 36, "compositions" should read --composition--;
Claim 2, line 52, "plamitate" should read --palmitate--;
Claim 22, line 28, "accordng" should read --according--.

Signed and Sealed this

Twentieth Day of December, 1988

*Attest:*

DONALD J. QUIGG

*Attesting Officer*     *Commissioner of Patents and Trademarks*